United States Patent
Gutierrez Villanueva (10) Patent No.: US 10,201,469 B2
(45) Date of Patent: Feb. 12, 2019

(54) UNISEX MASTURBATION DEVICE

(71) Applicant: Margarita Gutierrez Villanueva, Toledo (ES)

(72) Inventor: Jose Luis Gutierrez Villanueva, Toledo (ES)

(73) Assignee: Margarita Gutierrez Villanueva (ES)

( * ) Notice: Subject to any disclaimer, the term of this patent is extended or adjusted under 35 U.S.C. 154(b) by 407 days.

(21) Appl. No.: 15/102,933

(22) PCT Filed: Dec. 19, 2013

(86) PCT No.: PCT/ES2013/070899
§ 371 (c)(1),
(2) Date: Jun. 9, 2016

(87) PCT Pub. No.: WO2015/092081
PCT Pub. Date: Jun. 25, 2015

(65) Prior Publication Data
US 2016/0317380 A1 Nov. 3, 2016

(51) Int. Cl.
*A61H 19/00* (2006.01)
*A61H 21/00* (2006.01)
(Continued)

(52) U.S. Cl.
CPC ......... *A61H 19/32* (2013.01); *A61B 10/0058* (2013.01); *A61F 5/453* (2013.01);
(Continued)

(58) Field of Classification Search
CPC .......... A61H 7/00; A61H 7/008; A61H 19/00; A61H 19/30; A61H 19/32; A61H 19/34;
(Continued)

(56) References Cited

U.S. PATENT DOCUMENTS 8,926,498 B2 * 1/2015 Weng ................ A61H 19/32
600/38
9,949,866 B2 * 4/2018 Shubin, Sr. ............ A61F 5/453
(Continued)

FOREIGN PATENT DOCUMENTS

DE 202013104305 U1 12/2013
EP 1897519 A1 3/2008

OTHER PUBLICATIONS

International Search Report and Written Opinion for International Application No. PCT/ES2013/070899 (8 pages) (dated Aug. 18, 2014).

*Primary Examiner* — Colin W Stuart
(74) *Attorney, Agent, or Firm* — Lucas & Mercanti, LLP (57) ABSTRACT

Unisex masturbation device, having an external body, which is elongated and hollow and open at a first longitudinal extremity, and a longitudinal internal channel with an entry hole is provided. The external body is closed at a second longitudinal extremity opposite the first extremity and it has external shape and dimensions and is manufactured using a material with a level of rigidity and hardness suitable for its introduction into an adult's vagina, anus or mouth. In a particular embodiment, the unisex masturbation device comprises an internal body, which is elongated and hollow, housed inside the external body and wherein the internal channel is located. The device may be used simultaneously by various persons of different sexes.

8 Claims, 10 Drawing Sheets

(51) Int. Cl.
  *A61H 7/00* (2006.01)
  *A61F 5/453* (2006.01)
  *A61B 10/00* (2006.01)
  *A61H 23/02* (2006.01)

(52) U.S. Cl.
  CPC ............ *A61H 7/008* (2013.01); *A61H 19/30* (2013.01); *A61H 19/40* (2013.01); *A61H 19/44* (2013.01); *A61H 19/50* (2013.01); *A61H 21/00* (2013.01); *A61H 23/02* (2013.01); *A61H 2201/0107* (2013.01); *A61H 2201/0192* (2013.01); *A61H 2201/165* (2013.01); *A61H 2201/1692* (2013.01)

(58) Field of Classification Search
  CPC ........ A61H 19/40; A61H 19/44; A61H 19/50; A61H 21/00; A61F 5/451; A61F 5/453; A61F 5/4553; A61F 6/02; A61F 6/06; A61F 2006/048; A61B 10/0058
  USPC ........................ 600/38, 39, 41; 128/842, 917
  See application file for complete search history.

(56) References Cited

U.S. PATENT DOCUMENTS

| | | | |
|---|---|---|---|
| 2008/0065033 A1* | 3/2008 | Matsuura | A61B 10/0045 604/349 |
| 2008/0082028 A1 | 4/2008 | Blevins | |
| 2009/0171144 A1 | 7/2009 | Squicciarini | |
| 2013/0018222 A1* | 1/2013 | Miroshnichenko | A61H 19/32 600/38 |
| 2015/0164678 A1* | 6/2015 | Lee | A61F 5/41 600/38 |

\* cited by examiner

UNISEX MASTURBATION DEVICE

CROSS REFERENCE TO RELATED APPLICATION

This Application is a 371 of PCT/ES2013/070899 filed on Dec. 19, 2013, application is incorporated herein by reference.

TECHNICAL FIELD

The present invention is comprised within the field of sexual stimulation devices and more specifically, masturbation devices, massage devices or sex toys.

BACKGROUND OF THE INVENTION

In the current market, a multitude of different types of masturbation devices, for both males and females, may be found.

Said masturbation devices serve a specific function depending on the objective for which they are intended. In the case of male toys/masturbation devices there are an infinite number of different devices intended for introducing or massaging the penis, in which by means of one or more holes the penis may be introduced into the device and the masturbation may proceed. They are therefore, exclusively intended for male use.

Female devices existing on the market are adapted so that they may be introduced into the vagina or be used to massage the vagina externally, thus proceeding with the masturbation.

Masturbation devices available on the market are clearly differentiated for each sex and cannot be used on the different sexual organs of the opposite sex.

Male masturbation devices are normally open at a first extremity for the introduction of the penis and are open at the second extremity as well in order for the air to come out from the inside, thus making the use of the second extremity on the inside of the vagina or anus impossible, owing to suction danger, hence making said devices incompatible for both men and women.

Therefore, one single device cannot be used for sex of all types or even for all the sexual conditions of each individual, nor can they be used simultaneously by various persons of different sexes.

The present invention resolves the aforementioned problems.

DESCRIPTION OF THE INVENTION

The invention relates to a unisex masturbation device, which allows both men and women, regardless of their sexual condition (heterosexual, homosexual, bisexual), to masturbate and massage themselves or perform coitus, wherein one single device may be used individually or jointly by two persons. The device may be used to introduce the penis into the same or to introduce the device into the vagina, anus or mouth and it may even be used jointly by two persons.

The unisex masturbation device comprises an external, elongated, hollow body, open at a first longitudinal extremity; and a longitudinal internal channel with an entry hole for an adult's penis. The external body is closed at a second longitudinal extremity opposite the first extremity and it is provided with an external shape and dimensions and is manufactured using a material with a level of rigidity and hardness suitable for being introduced into an adult's vagina, anus or mouth.

In a first embodiment, the unisex masturbation device comprises an internal, elongated, hollow body, housed inside the external body, wherein the internal channel is located. The internal body is preferably removable. The internal channel of the internal body may have an exit hole located at the extremity opposite the entry hole. The internal body may have folds or protuberances, around the entry hole, which simulate a mouth with its tongue out.

The external body may assume the external shape of a bottle. In this case, it may further comprise a cap, which is adjusted to the first extremity of the external body.

The unisex masturbation device preferably comprises a system for regulating the air coming out from the inside of the device, which in turn, comprises an air regulation ring with at least one hole, which may be rotated so as to make it correspond to at least one hole made on the external body.

The internal body may comprise a number of annular sections for fastening the internal body to the external body. The internal body may also comprise at least one longitudinal projection to house at least one vibrating appliance.

In a second embodiment, the unisex masturbation device is manufactured as one single piece, taking on an external penis shape, with a chamber on its second extremity, which adapts itself to the shape of the gland and, in turn serves as an air chamber and semen reservoir. This embodiment of the device may additionally have folds or protuberances, around the entry hole, which simulate a mouth with its tongue out.

The internal surface of the internal channel is preferably designed to favor the stimulation of the penis.

An additional aspect of the present invention relates to a unisex masturbation assembly, which comprises two unisex masturbation devices according to any of the previous embodiments and one joining piece to connect the devices at equal extremities.

The present unisex masturbation device is valid for use alone or in company, regardless of sex or sexual condition, therefore making it possible to satisfy the sexual needs of both sexes and different sexual conditions.

This device promotes the practice of safe sex, since it may be used by two persons simultaneously, without exchanging fluids, thus avoiding possible risks of infection with sexually transmitted diseases (STD), by keeping the penis completely separated from the vagina, anus or mouth.

In addition, using it simultaneously in couple avoids the risk of unplanned pregnancy, since the semen stays located inside the device.

Moreover, the unisex masturbation device increases stimulation of the penis, given that its inside may have a multitude of shapes and sizes, to produce different sensations.

In addition, its external form is designed in different shapes and sizes to increase sensitivity and make masturbation more pleasurable by using it on the internal and external areas of the vagina, anus or mouth or by massaging the external area of the vagina, anus, mouth, testicles or penis, wherein it may be used as an external massage device for the sexual organs.

Regarding the internal size of the device, it may have different internal width measurements, in order to press the penis more or less, as well as different length measurements to adapt to different penis measurements, making its use possible regardless of the size and the thickness of the user's penis. Moreover, since the material is elastic or flexible, said material may adapt to the length or width of the male member.

With reference to the external size of the device, it may differ in height or width, so that the user may choose the measurement that suits him or her better, which may be another incentive for its use in persons with a small penis or persons with erection problems.

The possibility of manufacturing the device using just one elastic or flexible material, which may adapt itself to the different dimensions of the male member, is envisaged.

The device may be placed on the penis and fastened to the body by means of a fastening device, in order to facilitate its use by two persons at the same time.

In addition, the external design may vary in shape, in order to achieve different effects in the different cavities (vagina, anus or mouth).

It is also possible to use said device jointly, with a protection placed on the external portion as a cover, which in turn, improves hygiene when used individually or collectively and, in addition, its shape may vary in order to achieve distinct sensations and/or stimulations.

The external shape, which may be adopted by the device, always allows the introduction of the penis at one of its extremities and the introduction thereof into the vagina, anus, or mouth at the other extremity, so that both extremities serve as external massage devices for the sexual organs, wherein it may adopt real or geometric shapes and even shapes, which all together, turn the device into a discreet object in the form of a bottle or everyday objects, thus, preventing the external shape and the hole of the internal device from offending certain people, hence enabling it to be displayed for its sale, owing to its discreet shape, in business premises with access for minors, although it is exclusively intended to be sold to those of legal adult age.

The function of the present invention with regard to the male masturbation devices existing in the market is that it may be used on different organs, since the evacuation of the air from the inside takes place in the front portion of the device, unlike the existing devices, so there is neither suction danger nor exchange of fluids. In addition, said air evacuation function is performed by means of a controlled regulation system, i.e., by using it, is possible to choose the amount of air that comes out of the device through the different positions on an air regulation ring, and it is even possible to choose the closed position, thus increasing air pressure inside the device. The air regulation ring has a diameter slightly larger than the diameter of the external body where it is located. When turning this ring, a number of windows or holes of the ring coincide with the windows or holes in the base of the external body, thus making possible to control the air coming out from inside the device. Therefore, it will be possible to make the holes fully coincide (in an open position), partially coincide or not coincide (in a closed position), thus, controlling the air pressure inside the device at different levels, between open and closed, according to the user's preferences.

Male masturbation devices existing on the market are exclusively for male use alone (they are only designed for men to introduce their penises into them), while the present invention is designed for the penis to be introduced into the device and for the device to be introduced into the vagina, simulating female and male penetration.

Female masturbation devices (dildos and vibrators) existing on the market are designed to be introduced into the vagina or anus, but none of them has an entry hole to introduce the penis or an entry channel with a wrinkled surface or a surface with reliefs, intended to massage the penis. Therefore, female masturbation devices, which are completely closed at one of their extremities, with a cavity for the introduction of the penis in the other extremity and a conduct with a material and shape such that is, intended to proceed with male masturbation, do not exist on the market either.

The device also has specific designs on the lower extremity, where the penis introduction hole is located, which are designed in such a way that they create protuberances intended to massage the external area of the vagina, anus, mouth, testicles or penis, wherein the preferred shape is that of a mouth with its tongue out, which upon being rubbed against the aforementioned organs manages to simulate oral sex. These protuberant shapes may have multiple forms, whether realistic or geometrical, with the same aim, of using them as external massage devices for the sexual organs.

Likewise, the upper extremity of the external body may adopt a multitude of shapes and designs to produce the desired effect on the aforementioned organs, turning the device into a comprehensive toy to carry out the sexual fantasies of men and women (oral sex, male and female penetration, while always keeping the members used isolated from one another and preventing the exchange of body fluids).

One or more vibrating appliances available on the market may be introduced in order to make the device vibrate as a whole, both inside and outside, placing said vibrating appliances in the lateral hollows located inside the device, in hollows inside the fasteners or in the hollow existing in the upper extremity (neck of the bottle).

As far as the covers are concerned, it may also include a vibrating ring for the external portion. The fasteners of the internal body are there so that the piece remains fastened inside the device and so that the penis is pressed longitudinally when it comes into contact with the walls, thus increasing sensations during its use and fixing the internal piece to the external one, so that it does not become loose.

Furthermore, it must be emphasized that, by way of a function, the existing shape designed in the front portion, where the entry hole for the penis is located, has protuberant or wrinkled shapes in relief, which is preferably in the shape of a mouth with lips and its tongue out so as to successfully simulate oral sex in female and male users, by rubbing that specific portion of the device against the desired organ. Owing to its suitable texture and shapes, arousal will be achieved by means of massage or friction on the sexual organ.

The distinct advantages provided by the device are:
Enabling a female and a male masturbation device, which also includes a massage function to simulate oral sex, to be joined in one single device. The device may assume a multitude of external shapes and sizes but always has an open extremity to introduce the penis and a closed extremity to introduce such device into the vagina, anus or mouth.
The device may be made to vibrate, by means of one or various vibrators placed both inside and outside.
The device may be used individually or in couple.
The device prevents physical contact and fluid exchange, if used simultaneously by various users.
The device has a system with various air output regulation levels, with a closed position, to increase or decrease the internal air pressure.
It is a discreet device, given that it may adopt the external shape of everyday objects, such as a bottle, thus going unnoticed.

The device may be joined to another similar device through its own extremities by means of one of the joining means designed for this purpose, resulting in a double device, which may be used by two individuals of the same sex, either to introduce their penises into the free extremities or to introduce the free extremities into their vaginas, anuses or mouths.

BRIEF DESCRIPTION OF THE DRAWINGS

Below, a series of drawings are briefly described, which help us to better understand the invention and are expressly related to an embodiment of said invention, presented as a non-limitative example thereof.

DETAILED DESCRIPTION OF THE INVENTION

Figure 1:
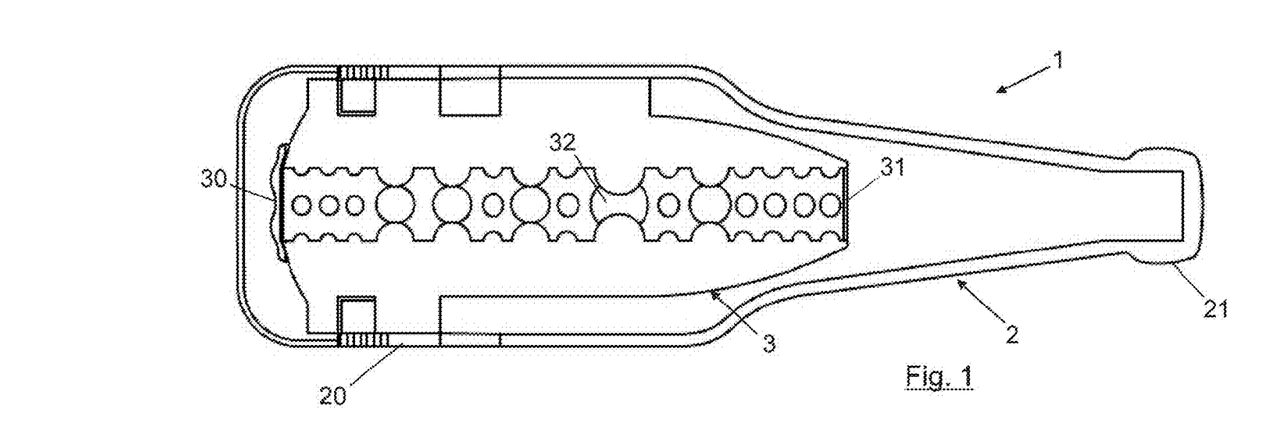
FIG. 1 shows, in a longitudinal section, a preferred embodiment of the unisex masturbation device, composed of two independent bodies (internal body and external body).
Figure 2:
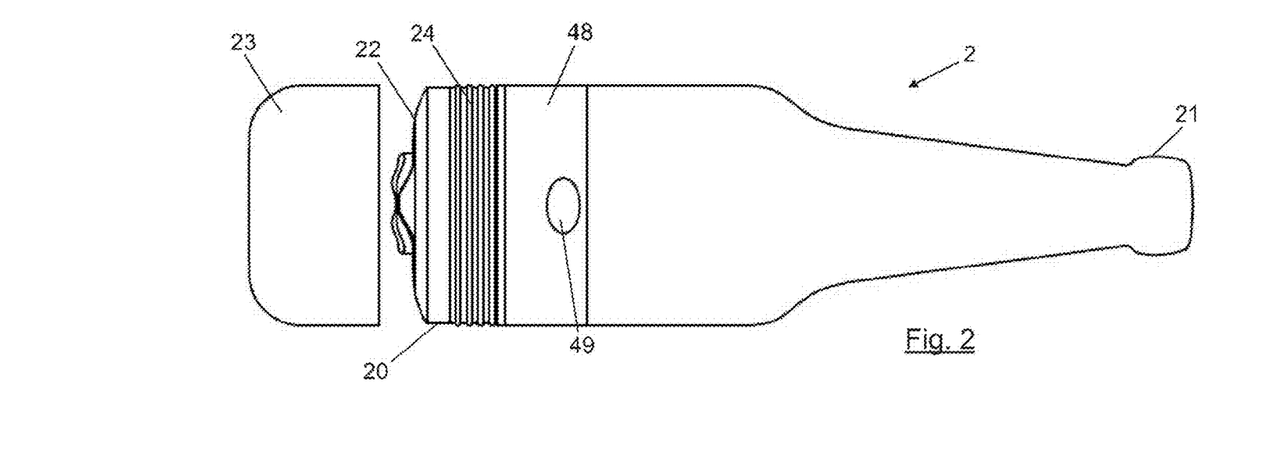
FIG. 2 shows a lateral view of the external body according to the embodiment of FIG. 1.
Figure 3:
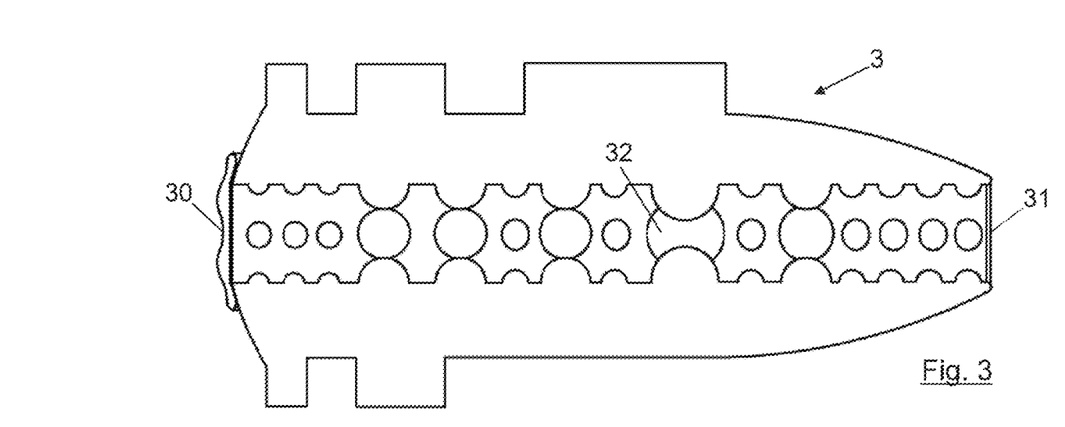
FIG. 3 shows a longitudinal section of the hollow internal body according to the embodiment of FIG. 1.

FIG. 1 shows a preferred embodiment of the unisex masturbation device 1, which comprises a hollow external body 2 made of rigid material, represented in FIG. 2 and a hollow internal body 3 made of elastic and/or flexible material, represented in FIG. 3.

The first extremity 20 of the external body 2 has a transversal section, which is larger than that of its second extremity 21. The first extremity 20 has an opening 22 for the insertion of the internal body 3, while the second extremity 21 is closed to prevent the penis coming into contact with any sexual orifice.

The internal body 3 has a conduct or channel 32 for the insertion of the penis. The channel may have distinct rugosities or any shape/relief, which favors the arousal of the penis, being made of the suitable soft and elastic material according to what is already known in this type of devices. On a first extremity, the channel has an entry hole 30 for the entry of the penis, and on a second extremity, it has an exit hole 31, either for the end portion of the penis to come out or for the air to come out. However, this exit hole 31 may be optional, since the channel 32 may be closed at that extremity.

In the embodiment shown in FIG. 2, the external body 2 is bottle shaped, in order to disguise the device 1. In this way, in this embodiment the external body 2 has a cap 23, which is adjusted to the first extremity 20 of the external body 2, hiding the protruding portion of the internal body 3. Said cap may be fastened to the external body 3 by means of a thread (24, 24') made on the first extremity 20 and on the cap 23, as shown in FIG. 4, or by any other fastening means.

In the embodiment shown in FIG. 3, an embodiment of the internal body 3 is shown, which is elongated in shape to adapt itself to the user's penis and to the internal portion of the external body 2.

Figure 4:
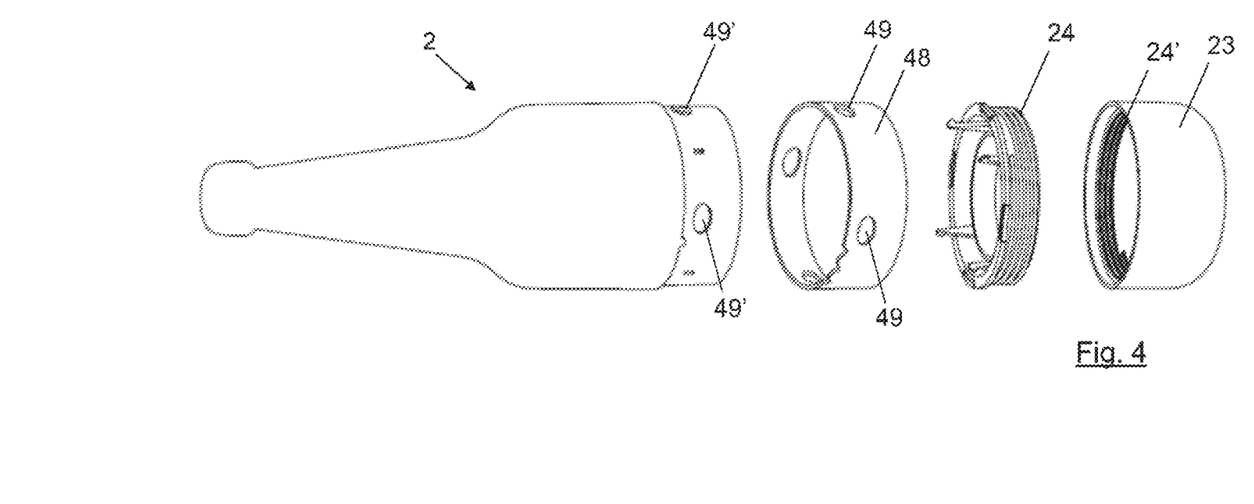
FIG. 4 shows an exploded view of an embodiment of the external body in the shape of a bottle.

FIG. 4 shows an exploded view of an embodiment of the external body 2 in the shape of a bottle, wherein the cap 23, which is coupled to the threaded piece 24, may be observed. In this way, the device would be even better disguised, since no hole for the insertion of the penis could be seen externally, thus resembling a bottle even more. In order to employ the device, the user should only unscrew the cap 23.

The external body 2 has an air regulation system, which comprises a controlled regulation mechanism, which makes it possible to select the amount of air coming out of the device by means of the different positions an air regulation ring 48 has, and even the closed position may be chosen, thus increasing the air pressure inside the device. The air regulation ring 48 has one or various holes 49 made in it. By turning the air regulation ring 48 said holes 49 may be made to correspond partially or fully with other similar holes made in the external body 2, in such a way that the air pressure inside the device may be regulated. The evacuation of air to the exterior may even be avoided, by turning the air regulation ring 48, so that the holes 49 and 49' do not correspond with each other (closed position). The holes (49, 49') are located in the front portion of the device 2, the closest to the first extremity 20, in order to evacuate the air contained inside this area, thus avoiding suction danger and fluid exchange.

Figure 5:
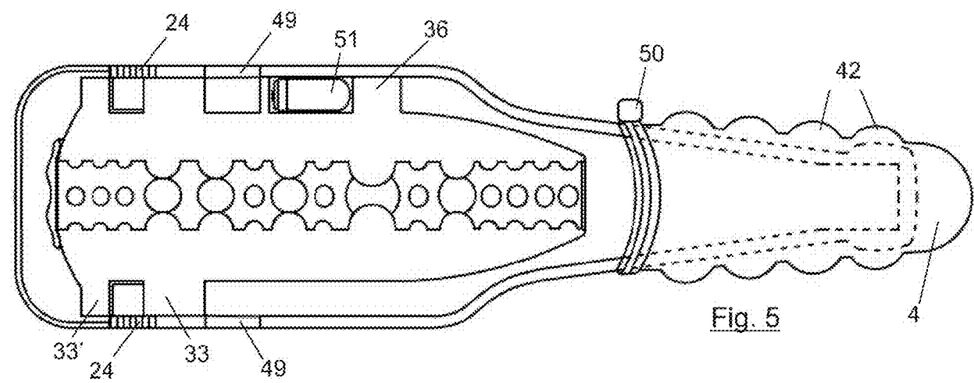
FIG. 5 shows the use of covers, which are placed over the extremity of the external body for improved hygiene.

The external body 2 may have different shapes or reliefs on its external surface in order to stimulate the sexual orifices (vagina and anus). Moreover, as shown in FIG. 5, the device 1 may also be used with protection, in the form of a cover 4, placed on the external portion of the device (over the second extremity 21 of the external body 2, which is normally introduced into the vagina, mouth or anus of another subject) in order to improve hygiene if used collectively. The cover 4 may adopt various shapes and reliefs in order to produce distinct sensations and/or stimulations in the mouth, vagina or anus of the subject. Thus, the particular embodiment shown in FIG. 5 shows a series of protuberances 42 to contribute to the stimulation. In another particular embodiment, grooves or furrows could be used instead or a combination thereof together with the protuberances 42. Furthermore, the grooves or furrows and/or the protuberances 42 could be made in the external body. Likewise, the device 1 may be used by placing a prophylactic on the penis to improve hygiene if the device 1 is going to be shared.

Figure 6:
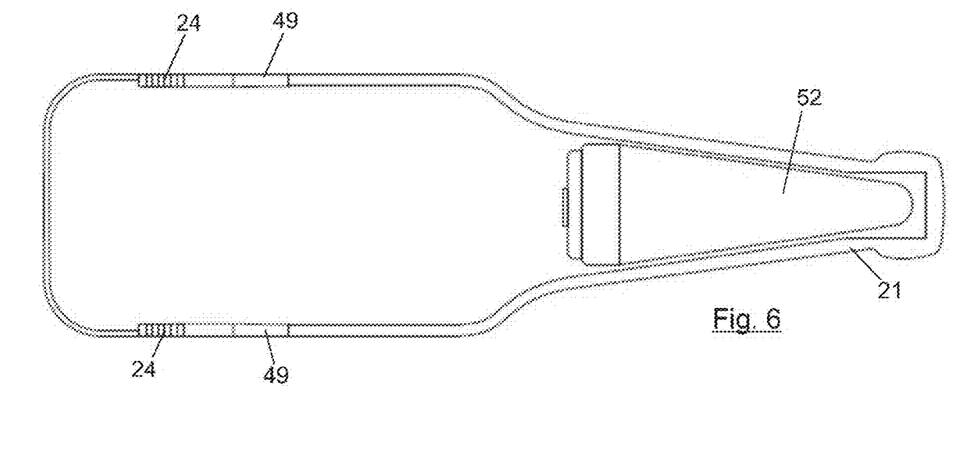
FIG. 6 represents the external body with a vibrating appliance inside it.

The device may be equipped with internal and external vibrating systems, incorporating vibrating appliances in the hollows the device has inside it and a vibrating device may also be incorporated on the exterior as a vibrating ring 50. FIG. 5 shows a vibrating appliance 51 applied inside a longitudinal projection 36 and other vibrating appliance 50, in the form of a vibrating ring, applied on the external portion of the external body 2, while FIG. 6 shows a vibrating appliance 52 applied inside the external body 2, which adapts to the form of its extremity 21. In this way, the device as a whole may become a comprehensive vibrator in order to increase stimulation.

Figure 7A:
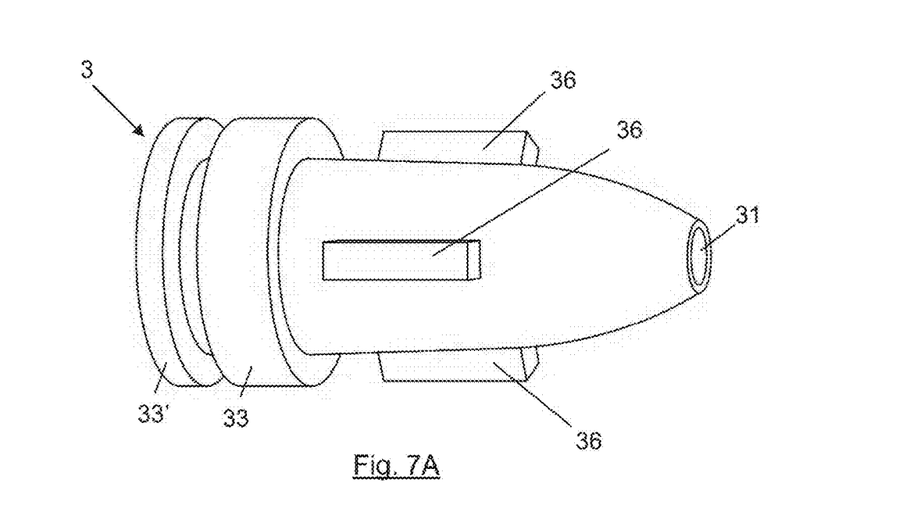
FIGS. 7A, 7B, 7C, 7D and 7E show a possible embodiment of the internal body.
Figure 7B:
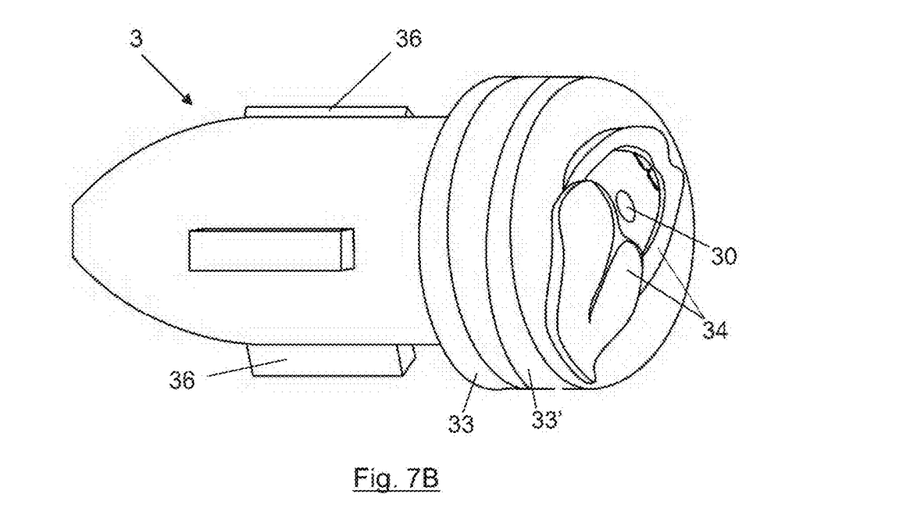
Figure 7C:
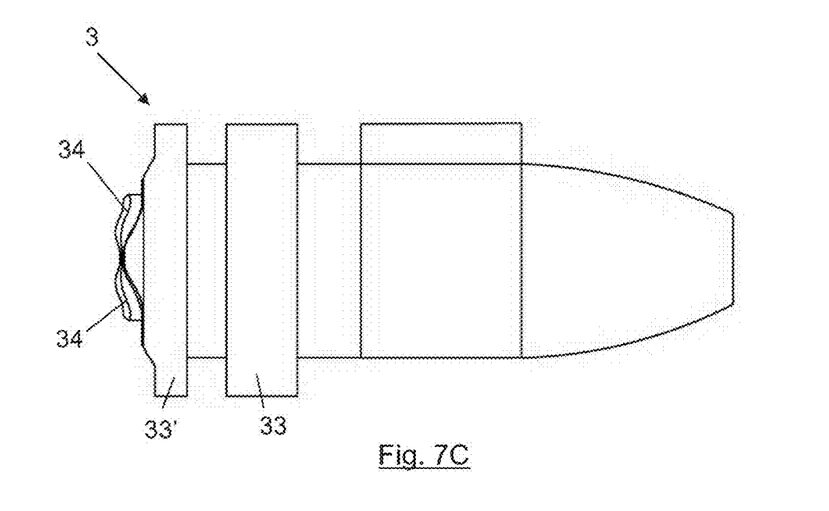
Figure 7D:
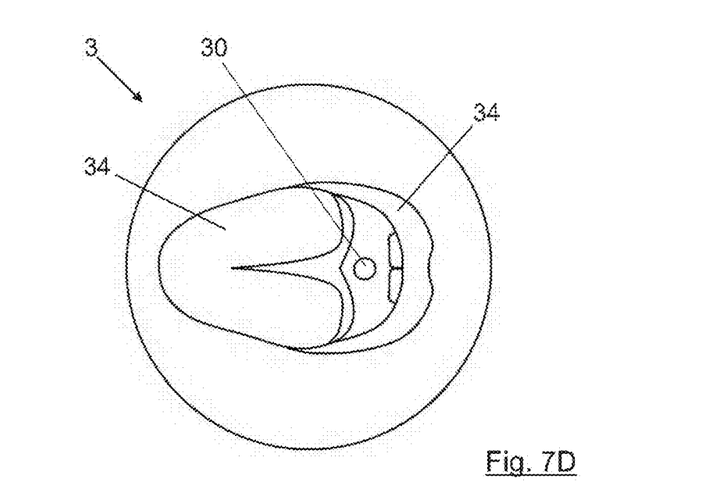
Figure 7E:
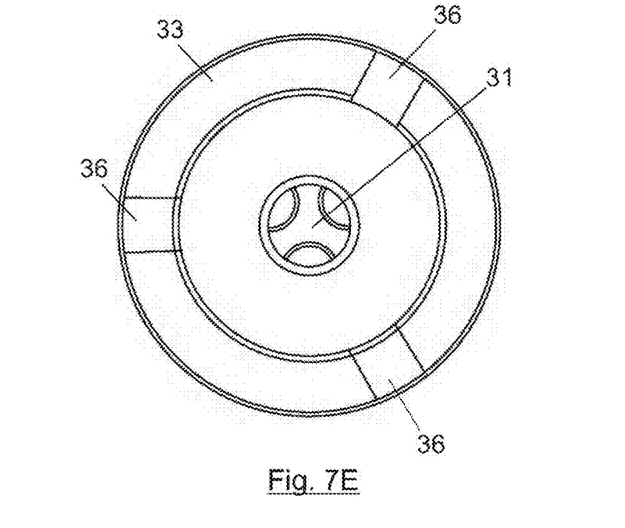

FIGS. 7A, 7B, 7C, 7D, and 7E show a possible embodiment of the internal body 3. FIG. 7A shows a perspective view of the internal body 3, wherein first 33 and second 33' annular section and a number of longitudinal projections 36 (in the example shown, three longitudinal pieces) can be seen. These annular sections (33, 33') serve to fasten the internal body 3 to the external body 2 (the longitudinal projections 36 may also serve this fastening function). The external body 2 has a protruding annular section, which is placed just between the annular sections (33, 33') of the internal body 3. This makes both bodies remain fixed and owing to the elasticity and flexibility characteristics of the internal body, it may be taken out or put inside manually by forcing said internal body with the fingers, although it cannot come out during use. The internal body 3 may have, folds or protuberances 34 around the entry hole 30 of the channel 32, as shown in FIGS. 7B and 7C, which simulate a mouth with its tongue out, in order to massage and/or stimulate the different sexual organs of the users by rubbing it against them, thus achieving the simulation of oral sex in both women and men. In this way, the entry hole will be in the shape of a mouth with its tongue out. FIG. 7D shows a front view of the entry portion, wherein the entry hole 30 with the protuberances 34 can also be seen. FIG. 7E represents a front view of the exit portion, wherein the exit hole 31, the longitudinal projections 36 and the first annular section 33 can be seen.

In turn, the internal body 3 may have distinct shapes or internal reliefs to stimulate the penis.

The external body 2 may be manufactured using materials of distinct hardness and rigidity, since it is designed to penetrate the sexual orifices, namely vagina, anus or mouth, the external material thus needing to be made out of a material more rigid than that of the internal body, since the internal body 3 of the device needs to have a lesser degree of hardness and rigidity, since it comes into contact with the penis and, in turn, it must be more elastic and flexible.

Figure 8:
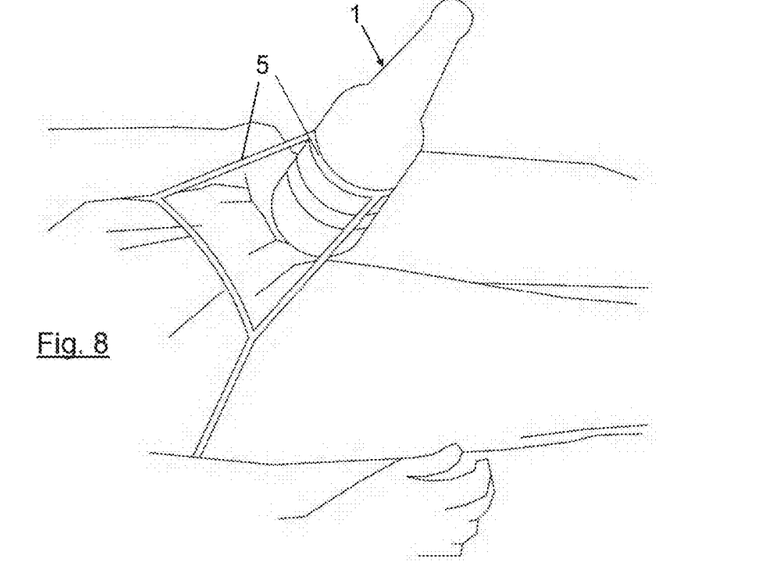
FIG. 8 shows the use of the masturbation device in the shape of a bottle with fastening means to fix it to the user's body.

An adjustment system, which may be slid to different settings, is in charge of keeping the device fixed to the penis in order to facilitate simultaneous use by two or more persons, without needing to hold it with your hand. In this way, the device may be placed on the penis and fastened to the body with a number of fastening means 5 in order to facilitate the use thereof by two persons at the same time. The fastening means may consist, for example, of a number of elastic bands, which, on the one hand, surround the external body 2 of the device 1 and, on the other hand, are adjusted to the user's waist, as shown in FIG. 8. Other possible and multiple embodiments of the fastening means 5 may be employed with the same aim of fastening the device 1 to the user's body, in order to facilitate the use thereof.

In the various embodiments shown until now, we have seen an internal body 3 introduced into an external body 2, wherein the internal body 3 is removable, which provides various advantages. On the one hand, the internal body 3 may be removed in order to proceed with its cleaning after using the device 1. The fact that the internal body may be removed from the external one enables different internal and external models that are compatible with each other to be exchanged. Moreover, the internal body 3 may be heated or cooled down before using the device to obtain a more pleasurable sensation after use.

Figure 9A:
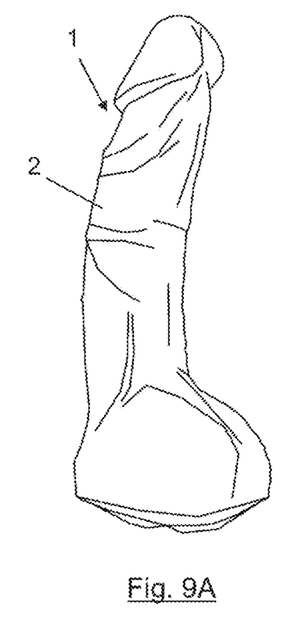
FIGS. 9A, 9B and 9C show another preferred embodiment of the unisex masturbation device, composed by one single body instead of two.
Figure 9B:
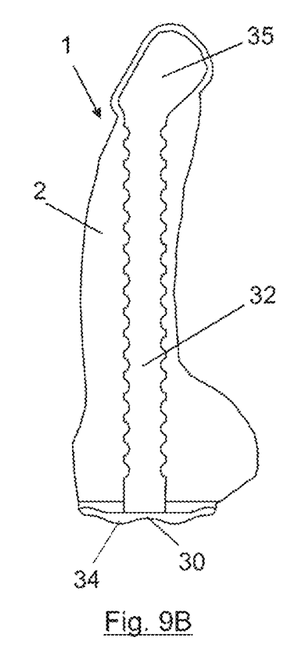
Figure 9C:
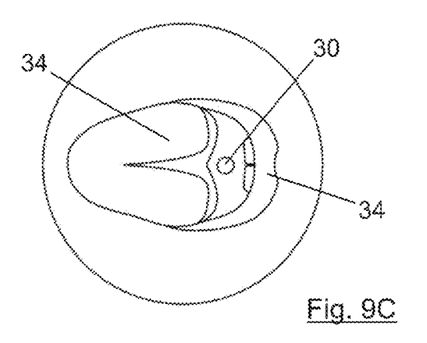

In another preferred embodiment, rather than having two bodies the device 1 is manufactured in one single piece, using a material with different degrees of hardness, rigidity, elasticity and flexibility on the outside and inside. A possible embodiment is shown in FIGS. 9A, 9B and 9C, wherein the device 1 assumes the external shape of a penis in order to increase visual stimulation for users. FIG. 9A shows the external aspect of the device, formed by a hollow external body 2. FIG. 9B shows a longitudinal section wherein an internal channel 32 is shown, where the user introduces his penis, through the entry hole 30. The channel 32 has a number of reliefs or protuberances along its length, in order to stimulate the penis. The channel preferably has an initial section, which is narrower than the end section. On its other extremity, the channel 32 widens in a chamber 35, in order to adapt to the shape of the gland, serving in turn as an air chamber and semen evacuation chamber, in case the user does not use a prophylactic. FIG. 9C shows a lower view of the device, wherein the entry hole 30 and folds or protuberances 34, which simulate a mouth with its tongue out, can be seen.

Figure 10:
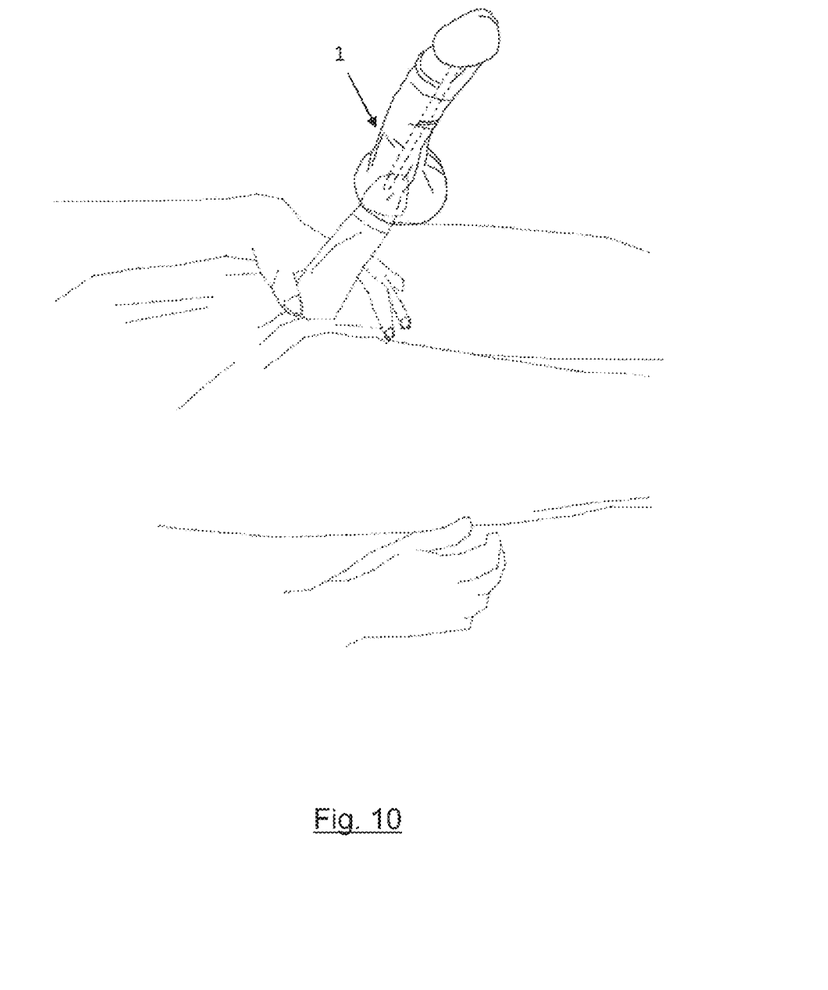
FIG. 10 shows the use of the device shown in FIGS. 9A, 9B and 9C.

FIG. 10 illustrates the use of the device 1 shown in FIGS. 9A, 9B and 9C. The result of this preferred embodiment would be a hollow body with an external shape of a penis, with an internal channel with reliefs or protuberances open at the entry hole 30 and closed at its other extremity, wherein the user's penis has been introduced.

Figure 11A:
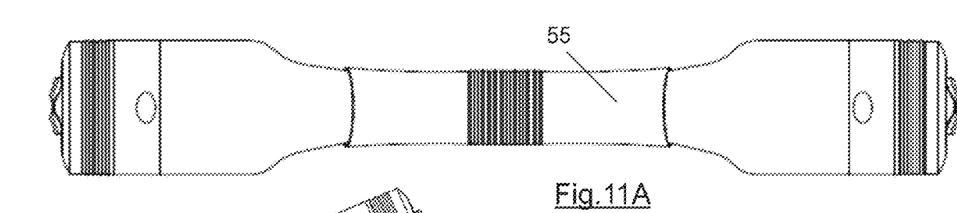
FIGS. 11A and 11B show the joining of two similar devices by means of their narrow extremities, employing a joining piece as shown in FIG. 11C.
Figure 11B:
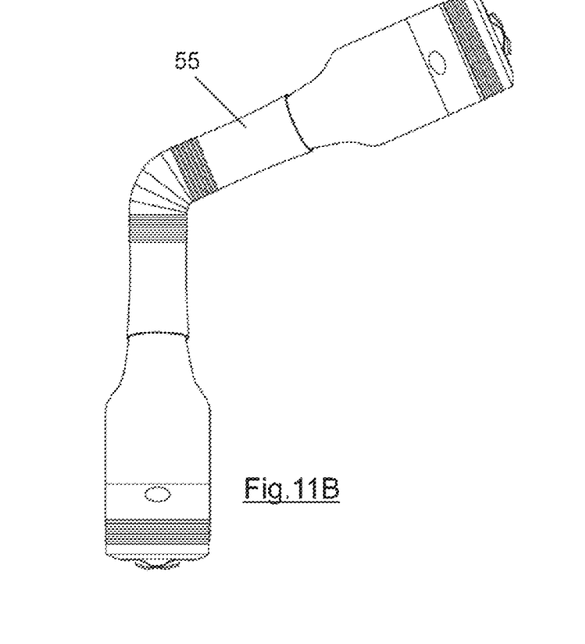
Figure 11C:
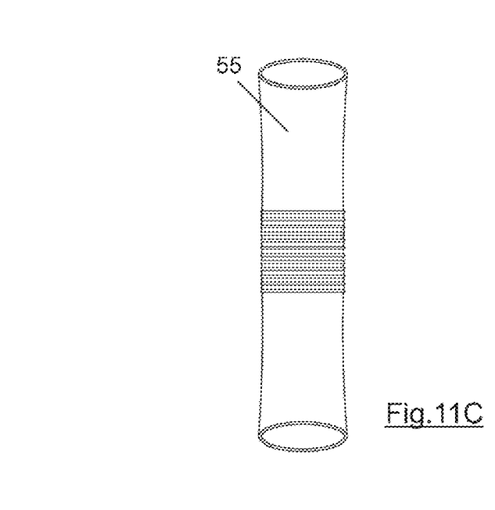
Figure 12A:
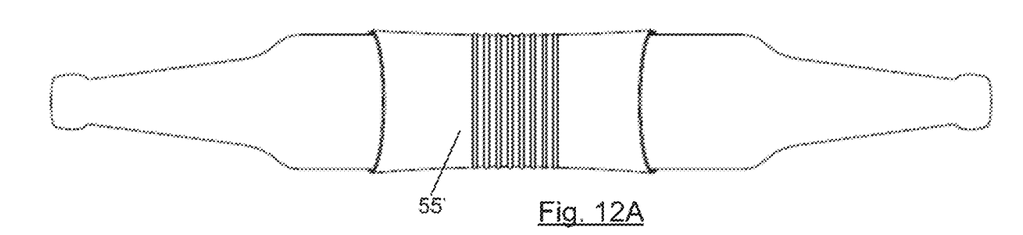
FIGS. 12A and 12B show the joining of two similar devices by means of their wide extremities, employing a joining piece as shown in FIG. 12C.
Figure 12B:
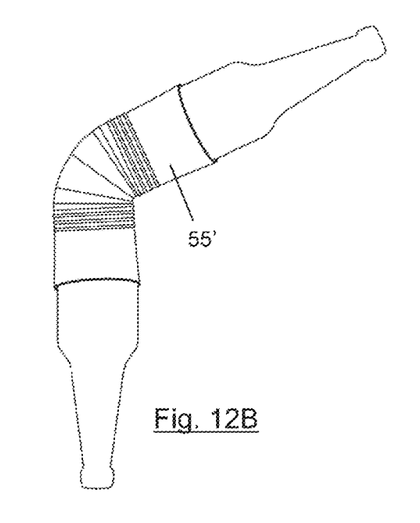
Figure 12C:
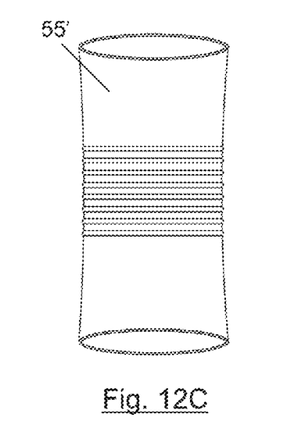

Two devices may be joined with the help of a joining piece, which enables two persons of the same sex to use them simultaneously, obtaining two entry holes for penises (FIGS. 11A and 11B) in the assembly or two extremities to be introduced into vaginas, anuses or mouths (FIGS. 12A and 12B). Said joining pieces (55, 55'), shown in FIGS. 11C and 12C, may be flexible, such as bellows, so that the assembly formed by the two devices joined to each other adopts different positions and is more comfortable or the users may adopt different positions or sexual postures. The joining piece (55, 55') is adapted to the extremities of the external bodies 2 of both devices 1, either to the first extremities 20 (wider joining piece 55') or to the second extremities 21 (narrower joining piece 55).

The invention claimed is:

1. Unisex masturbation device, which comprises:
   an external body, which is elongated and hollow, open at a first longitudinal extremity and closed at a second longitudinal extremity opposite the first longitudinal extremity and with an air regulation system for regulating air pressure inside the device;
   an elongated and hollow internal body, housed inside the external body, and having an internal longitudinal channel with an entry hole for an adult's penis;
   wherein, the external body has external shape and dimensions and is made of a rigid material and is suitable for introduction into an adult's vagina, anus or mouth, the first longitudinal extremity of the external body having a transversal section larger than a transversal section of the second longitudinal extremity; and the air regulation system comprises an air regulation ring with at least one hole that is adapted to be turned in order to make the at least one hole of the air regulation ring correspond with at least one hole in the external body.

2. The Unisex masturbation device according to claim 1, wherein the internal body is removable.

3. The Unisex masturbation device according to claim 2, wherein the internal longitudinal channel of the internal body has an exit hole located at an extremity opposite the entry hole.

4. The Unisex masturbation device according to claim 3, wherein the internal body has folds or protuberances around the entry hole which simulate a mouth with a tongue out.

5. The Unisex masturbation device according to claim 4, which comprises a cap that removably attaches to the first longitudinal extremity of the external body.

6. The Unisex masturbation device according to claim 2, wherein the internal body comprises annular sections for fastening the internal body to the external body.

7. The Unisex masturbation device according to claim 2, wherein the internal body comprises at least a hollow longitudinal projection to house at least one vibrating appliance.

8. The Unisex masturbation device according to claim 1, wherein the air regulation ring is adapted to be turned such that the at least one hole of the air regulation ring corresponds partially, fully or does not correspond with the at least one hole of the external body.

* * * * *